Figure 1:
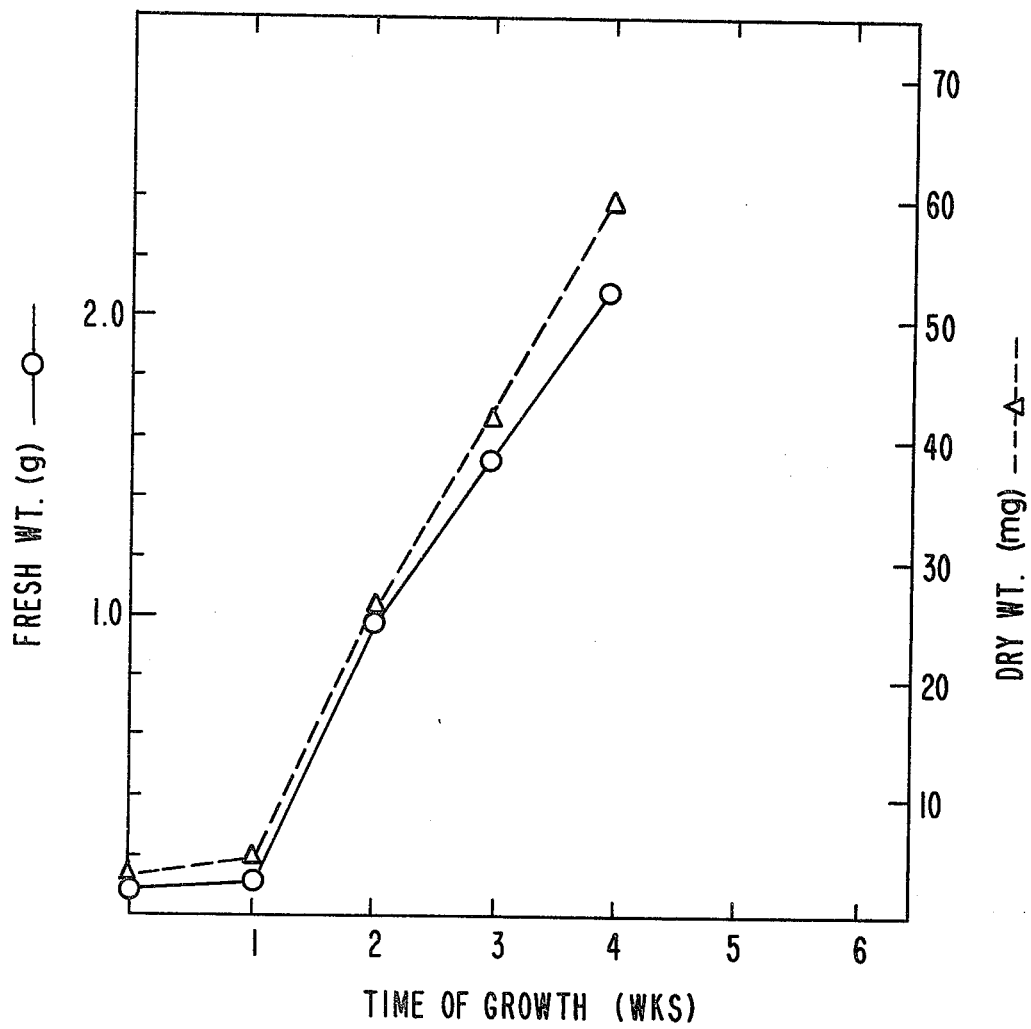

United States Patent [19]

Kinsella et al.

[11] 4,306,022

[45] Dec. 15, 1981

[54] COCOA BEAN CELL CULTURE

[75] Inventors: John E. Kinsella; Chee H. Tsai, both of, Ithaca, N.Y.

[73] Assignee: Cornell Research Foundation, Inc., Ithaca, N.Y.

[21] Appl. No.: 129,434

[22] Filed: Mar. 11, 1980

[51] Int. Cl.$^3$ .......................... C12N 5/02; C12P 7/64
[52] U.S. Cl. ................................. 435/134; 435/240; 435/241
[58] Field of Search ....................... 435/240, 241, 134

[56] References Cited

PUBLICATIONS

Jalal et al., Chemical Abstracts 87: 0148689y (1977), p. 298.
Radwan et al., "The Lipid of Plant Tissue Cultures", Advances in Lipid Research 14, (1976) 171-210.
Jones, "Plant Cell Culture and Biochemistry: Studies for Improved Vegetable Oil Production", Industrial Aspects of Biochemistry, Fed. Eur. Biochem. Soc., Amsterdam (1974).
Stearns et al., Phytochemistry, 14 (1976) 619-622.
Stumpf et al., Lipids, 12 (1977) 120-124.
Gamborg et al., Experimental Cell Research, 50 (1968) 151-158.
Moore et al., Plant Physiol., 53 (1974) 261-265.
Jalal et al., Phytochemistry, 16, 1377-1380 (1977).
Reynolds et al., "Plant Cell Lines", Methods in Enzymology, vol. LVIII, Academic Press, New York, 478-482 (1979).

Primary Examiner—Esther M. Kepplinger
Attorney, Agent, or Firm—Jones, Tullar & Cooper

[57] ABSTRACT

The invention relates to culturing cocoa bean cells in the presence of a cocoa bean cell culture growth supporting medium for a time and at a temperature sufficient to produce a metabolite, e.g. triglyceride species similar to those normally found in cocoa butter and isolating said metabolite.

4 Claims, 2 Drawing Figures

GROWTH CURVE OF COCOA CALLUS AT
TEMP. 30° C ON I-B5 AGAR.

FIG. I

GROWTH CURVE OF COCOA SUSPENSION CULTURE IN MS
LIQUID MEDIUM AT 25°C. SHAKING SPEED: 120 RPM

COCOA BEAN CELL CULTURE

BACKGROUND OF THE INVENTION

The products of the cocoa bean, i.e. cocoa, chocolate, and cocoa butter, originally developed by the Aztecs and adopted by the Spanish, are more prized today than ever, Unfortunately, the cocoa tree *Theobroma cacao* grows only in tropical regions 10°–15° N & S of the equator. The productivity of the cocoa tree is limited and expansion in production is slow. Further, political changes are affecting the reliability of supply, as well as the quality of the product.

General information on the cocoa bean and chocolate can be found in the books: Cooke, L. R., "Chocolate Production and Use", Magazine for Industry, New York (1963) and Minifie, B. W., "Chocolate, Cocoa and Confectionary: Science and Technology", Churchill, London (1970).

Cocoa butter is the premium confectionary fat because of its special physical properties, its unique taste and flavor. There is an increasing demand for cocoa butter and though some reasonable imitations or extenders are available, their use is limited by regulatory as well as technical problems. When cocoa butter is mixed with these imitation butters they form mixtures with inferior softening and melting characteristics as compared to pure cocoa butter.

While there are numerous publications on the unique composition and structure of cocoa butter triglycerides and their economically important physical properties, there is a dearth of information concerning the biosynthesis of cocoa bean lipids.

The ripe bean has one of the highest lipid contents (55–60 percent fat) of any occurring natural product. This is preponderantly 98+% triglyceride with 1–2% polar lipids [Parsons et al., *Am. Oil Chem. Soc.*, 46:425 (1969)].

The fatty acid composition of cocoa butter has been reported. Palmitic acid, (C16), stearic acid (C18), oleic acid (C18:1) and linoleic acid (C18:2) account for 26, 35, 34 and 3 percent of the total fatty acids respectively; [Jurriens et al, *J. Am. Oil Chem. Soc.*, 47:344 (1970); Kavanagh et al, *J. Am. Oil Chem. Soc.*, 42:9 (1965); Iverson, *J. Assoc. Off. Anal. Chem.*, 55:1319 (1972)].

The triglyceride composition of cocoa butter has been reported by many investigators; [Vander Val, *J. Amer. Oil Chem. Soc.*, 37:18 (1960); Coleman, *J. Amer. Oil Chem. Soc.*, 38:685 (1961); Subbaram et al, *J. Am. Oil Chem. Soc.*, 41:445 (1964); Chacko et al, *J. Am. Oil Chem. Soc.*, 41:843 (1964); Jurriens et al, (1965), supra]. There is general agreement on the triglyceride composition of cocoa butter. The stereospecific distribution of the fatty acids in cocoa butter triglycides (99% of total lipid) was reported by several workers; [Jurriens et al, (1965) supra; Youngs, *J. Am. Oil Chem. Soc.*, 38:62 (1961); Feuge et al, *J. Am. Oil Chem. Soc.*, 50:50 (1973)]. Oleic acid and linoleic acid are located exclusively on Sn-2 ($\beta$) whereas palmitic acid and stearic acid are equally distributed on SN-1 and SN-3 ($\alpha,\alpha'$).

Of most significance, however, is the marked non-random distribution of these fatty acids in the glycerides. Cocoa butter is unique because it is preponderantly composed of three triglyceride species—2-oleodipalmitin, POP (15%); 2-oleodistearin, SOS (25%), and 2-oleopalmitostearin, POS (40%). Thus 80% of the triglycerides are symmetrical (SUS type), and it is these that account mostly for the desirable physical properties of cocoa butter.

The hardness (fatty acid composition) of cocoa butter varies with mean daily temperature during growth; Alvin et al *Revista Theobroma*, 2:3 (1972). Winter crop cocoa developing in regions with a lower mean temperature produced cocoa butter of higher iodine value (softer). This was confirmed by Lehrian [Ph. D. Dissertation, Penn State University, (1978)] who studied changes in composition and melting characteristics of cocoa butter in relation to the state of maturity of cocoa beans and temperatures. It was reported that cocoa lipids progressively accumulated in maturing cocoa seeds from 120 days through 160 days after pollination. The butter from pods grown at higher temperatures had slightly more palmitate and stearate and 3% less oleate (harder). This phenomenon is consistent with the observation of other plants in tissue culture showing that lower growth temperatures increases the biosynthesis of unsaturated fatty acids; [Radwan et al, *Adv. in Lipid Res.*, 14:171, Academic Press (1976)].

There is abundant information concerning the synthesis of lipids in certain plants (soy, avocado, corn, safflower, pea) and this has recently been reviewed in comprehensive volumes by Hitchcock "Plant Lipid Biochemistry", Academic Press, N.Y. (1971) and Galliard and Mercer "Recent Advances in the Chemistry and Biochemistry of Plant Lipids", Academic Press, N.Y. (1975). Noteworthy is the absence of any information on the biosynthesis of cocoa butter.

Limited research has been done on exploiting plant cell cultures for their capacity to produce useful metabolities. Thus, certain cells in culture have been shown to synthesize aromatics and essential oils, Camborg, *Expl. Cell Res.*, 50:151 (1968).

Until recently, plant cell suspension cultures has not been employed extensively for studies related to lipid metabolism. The literature on this subject was reviewed by Radwan et al., *Adv. in Lipid Res.*, 14:171, Academic Press (1976). Moore et al., *Ph. Physiol.*, 53:261 (1974) have described a number of parameters involving the use of soybean suspension cells. Stearns et al., *Phytochem.*, 14:619 (1975), have examined the capacity of soybean suspension cells to incorporate acetate into fatty acids as well as the effect of growth hormones on lipid biosynthesis. Stumpf et al., *Lipids* 12:120 (1977), demonstrated that soybean cell suspension actively absorbed exogenous (C16 and C18) fatty acids desaturated them and converted them into triglycerides typical of soybean oil. The limited number of plant tissues examined in culture did not accumulate triglycerides under the conditions used, though Jones, *Industrial Aspects of Biochem.*, Amsterdam, P. 813 (1974), has reported that an increased synthesis of triglycerides occur with the induction of embryogenesis in cultures of rape tissue.

The techniques used for all culture are adapted from microbiological techniques and entail growing sterile tissue or cells in sterile nutrient media. Gamborg et al., "Paint Tissue Culture Methods" Nat'l Res. Comm., Saskatoon, Canada (1975), have recently described the experimental techniques used in plant tissue culture. The plant tissue to be cultured is sterilized, usually with sodium hypochlorite solution, and after washing is placed in sterile culture medium under aseptic conditions. The medium contains all of the known nutrients required for plant cells. The requirements vary with different plant species but generally sucrose or glucose, inorganic nitrogen (salts), some amino acids, the major and minor (trace) mineral elements, vitamins, and some auxins are included. The appropriate medium has to be determined for each plant species but some universal media are now available. In some instances media in which other cells have been grown contain stimulatory compounds which aid the establishment of primary cultures [Street et al., "*Les cultures de Tissues de Plants*", Colloq. N193 p. 17, CNRS, Paris (1971)].

DESCRIPTION OF THE INVENTION

This invention relates to culturing cocoa bean cells in the presence of a cocoa bean cell culture growth supporting medium for a time sufficient and at a temperature sufficient to produce metabolic lipids and them isolating the resulting lipids. It is noted that is employed herein the term "culturing cells" is generally employed to encompass both tissue culture (e.g. callus growth) and cell culture (e.g. cell suspension culture). Likewise "cells" is generally employed to include both cells and plant tissue which comprise cells.

In the process of the invention cocoa bean cells (e.g. obtained from the cotyledon) are tissue cultured in the presence of (in or on depending on the consistency thereof) a cocoa bean cell growth supporting medium for a time sufficient and at a temperature sufficient to produce metabolic lipids. The cells may be cultured on a solid, semi-solid medium (e.g. agar based) to promote callus growth or in a liquid suspension medium which supports cell growth. Alternatively both callus and cell growth techniques can be used seriatum. When desired continuous passage of the cell line can be accomplished by techniques known in the art.

Generally, a useful class of cocoa bean cell growth supporting media are those media known in the art to support soybean, tissue or cell cultures; [for example, see Gamborg et al. (1975 supra); Stump et al., *Lipid*, 12:120 (1977); Gamborg et al., *Expl. Cell Res.*, 50:151 (1968); Moore, *Pl. Physiol.*, 51:529 (1973); Moore et al., *Pl. Physiol.*, 53:261 (1974); Nothelfer et al., *Biochem. Biophys. Acta.*, 489:370 (1977); and Wilson et al., *Lipids*, 13:504 (1978)].

The temperatures at which the cell cultivation is conducted to provide lipids is not unduly critical, beyond the limitation that the temperature employed must be a temperature at which cell propagation occurs. It is noted, however, that temperature does affect the nature of the lipid formed, especially the amount of unsaturated fatty acid contained therein, much in the same way that it has been shown the temperature affects the lipid composition of cocoa beans grown in nature. Typically the solid or semisolid supported callus cultures are mentioned at a growth supporting temperature between about 20° C. and about 35° C., preferably between about 28° C. and about 32° C. Typically the suspension cell cultures are maintained at a growth supporting temperature between about 23° C. to about 35° C., preferably between about 25° C. to about 32° C.

The lipids formed in the process of this invention comprises triglycerides having an SUS configuration, i.e. having a saturated fatty acid in the SN-1 and SN-3 positions with an unsaturated fatty acid in the SN-2 position. As in cocoa butter obtained from the plant the fatty acids principly comprise palmitic acid and stearic acid, while the unsaturated acids comprise oleic acid and limoleic acid, the oleic acid, present being in quantities substantially larger than linoleic acid.

The lipids are isolated from the cell culture by techniques known to the lipid chemist, e.g. extraction with warm organic solvent such as hexane followed by evaporation of the solvent.

The lipids isolated from the cell cultures of this invention may be useful as cocoa butter extenders, food additives, in cosmetic preparations, and as lubricants.

The appropriateness of a particular tissue culture medium, or component thereof, and/or temperature can be determined by a screening series where one or more parameter is changed and the resultant affect upon the viability or cell preparation observed.

There follows an example which is to be considered illustrative rather than limiting. All parts and percentages herein are by weight unless otherwise specified. All temperatures are degrees Centigrade unless otherwise specified.

EXAMPLE

Immature cocoa pods were sterilized with 1% sodium hypochloride and washed with sterile distilled water. They were then cut open aseptically and small pieces of cotylendons were transferred to an agar medium [Gamborg et al., (1975) supra-1B5] with 2, 4-D and kinetin hormones, containing the following components:

| Macronutrients | mM |
| --- | --- |
| $NaH_2PO_4 \cdot H_2O$ | 1.0 |
| $KNO_3$ | 2.5 |
| $MgSO_4 \cdot 7H_2O$ | 1.0 |
| $(NH_4)_2SO_4$ | 1.0 |
| $CaCl_2 \cdot 2H_2O$ | 1.0 |
| Micronutrients | $\mu M$ |
| KI | 4.5 |
| $H_3BO_3$ | 5.0 |
| $MnSO_4 \cdot H_2O$ | 6.0 |
| $Na_2MnO_4 \cdot H_2O$ | 1.0 |
| $2nSO_4 \cdot 7H_2O$ | 7.0 |
| $CoCl_2 \cdot 6H_2O$ | 0.1 |
| $CuSO_4 \cdot 5H_2O$ | 0.1 |
| Ferric EDTA | 100 |
| Vitamins | PPM |
| Inositol | 100 |
| Nicotinic acid | 1.0 |
| Pyridoxime . HCl | 1.0 |
| Thyamine . HCl | 10.0 |
| Sucrose | 20g/l |
| 2,4-D | 1.0 ppm |
| Kinetin | 0.2 ppm |
| Agar | 0.8% |
| pH | 5.5 |

These cultures were incubated at 30° C. in a moisture-controlled incubator. Substantial callus formed in 3 to 4 weeks. The growth was monitored according to fresh weight and dry weight of callus. FIG. 1 depicts the growth results.

The lipids were isolated from the resultant callus tissue culture with chloroform methanol mixture (2:1 vol/vol).

The total lipid content of the callus culture was determined to be 10% on a dry weight basis. It contained 34% palmitic acid, 24% stearic acid, 34% oleic acid and 8% linoleic acid. The fatty acid composition is quite similar to commercial cocoa butter except that the proportion of linoleic acid is slightly higher.

Tissue cultures at higher temperatures reduce the amount of linoleic present.

A loop of the above callus tissue was then inoculated into 40 ml of MS (Murashiqe & Skoog) suspension culture medium with Kinetin [see Gamborg et al., (1975), supra]. The culture medium included the components:

| Macronutrients | mM |
|---|---|
| NH$_4$NO$_3$ | 20.6 |
| KNO$_3$ | 18.8 |
| CaCl$_2$ . 2H$_2$O | 3.0 |
| MgSO$_4$ . 7H$_2$O | 1.5 |
| KH$_2$PO$_4$ | 1.25 |
| Micronutrients | μM |
| KI | 5.0 |
| H$_3$BO$_3$ | 100 |
| MnSO$_4$ . 4H$_2$O | 100 |
| 2nSO$_4$ . 7H$_2$O | 30 |
| Na$_2$MoO$_4$ . 2H$_2$O | 1.0 |
| CuSO$_4$ . 5H$_2$O | 0.1 |
| CoCl$_2$ . 6H$_2$O | 0.1 |
| Ferric EDTA | 100 |
| Vitamins | PPM |
| Inositol | 100 |
| Nicotinic acid | 0.5 |
| Pyridoxime . HCl | 0.5 |
| Thyamine . HCl | 0.1 |
| Sucrose | 30g/l |
| Kinetin | 0.5 ppm |
| pH | 5.8 |

Figure 2:
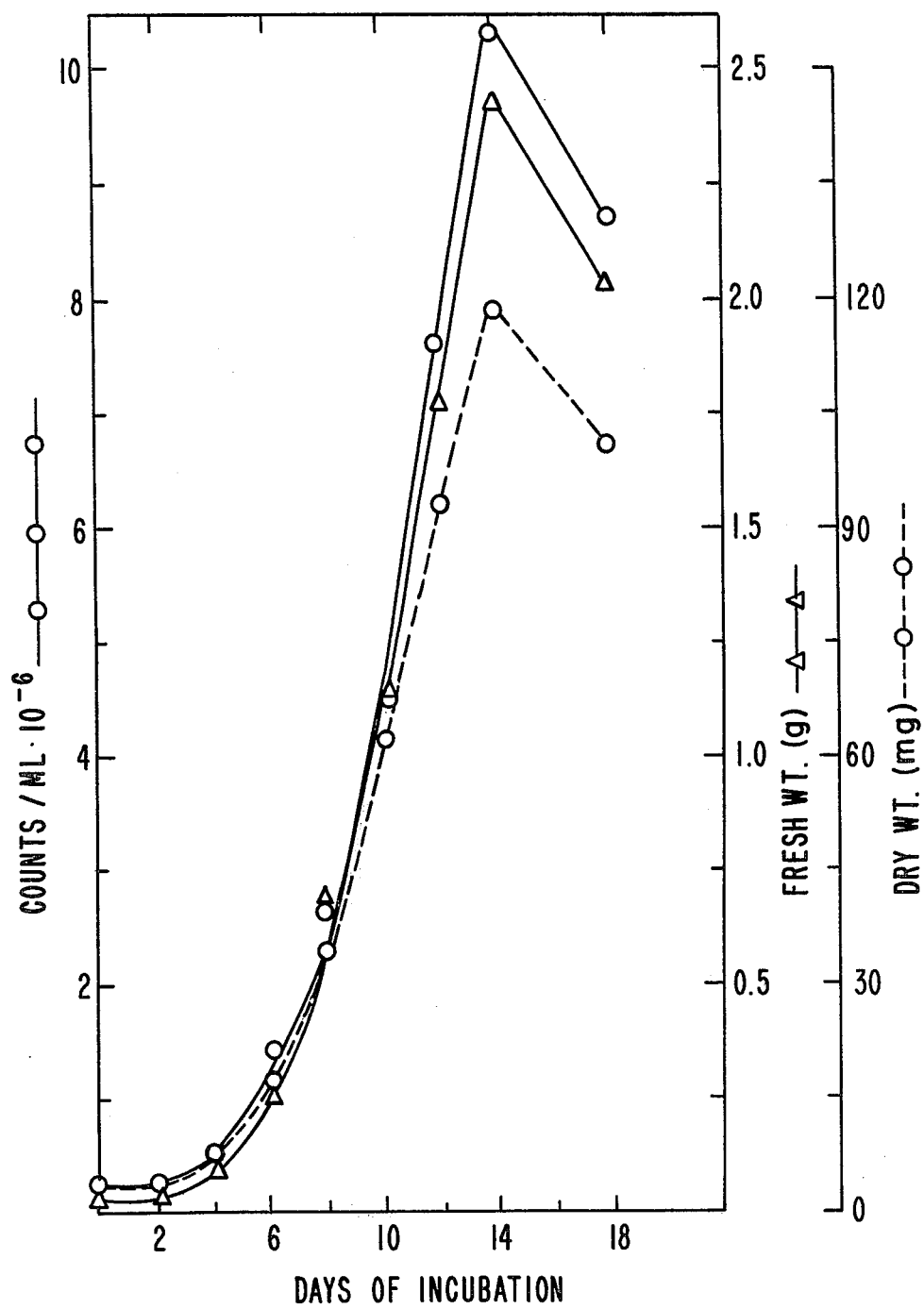

The 40 ml of medium was contained in a 125 ml Erlemeyer flask as previously described for soybean culture (supra). The inoculum was incubated at 25° C. in the dark with continuous shaking at 125 rpm for 7-14 days. The growth of cells in the liquid medium was monitored according to cell number determined with haemocytometer; by fresh weight and by dry weight. FIG. 2 depicts the growth results.

Lipids isolated from the cell culture showed fatty acid contents and structural configurations similar to those from cocoa beans.

We claim:

1. A method of producing SUS triglycerides which comprises cultivating cocoa bean cells by suspension cell culture in the presence of a cocoa bean cell growth supporting medium for a time and at a temperature sufficient to propagate said cells thereby forming SUS triglyceride metabolites and separating said triglycerides from the cell culture.

2. A method as in claim 1 wherein the fatty acid contained in said triglycerides comprise palmitic acid, stearic acid, oleic acid and linoleic acid.

3. A method as in claims 1 or 2 wherein cocoa bean cotyledon is first grown on a solid or semisolid medium to form callus and then the callus resultant is subsequently subjected to said suspension cell culture.

4. A method as in claim 3 wherein the solid or semisolid medium is agar based.

* * * * *